United States Patent
Lee

(10) Patent No.: US 8,876,829 B2
(45) Date of Patent: Nov. 4, 2014

(54) ADJUSTABLE APPARATUS AND METHODS FOR INSERTING AN IMPLANT

(71) Applicant: Amicus Design Group, LLC, Arlington, TX (US)

(72) Inventor: Randall F. Lee, Arlington, TX (US)

(73) Assignee: Amicus Design Group, LLC, Arlington, TX (US)

( * ) Notice: Subject to any disclaimer, the term of this patent is extended or adjusted under 35 U.S.C. 154(b) by 0 days.

(21) Appl. No.: 14/025,068

(22) Filed: Sep. 12, 2013

(65) Prior Publication Data
US 2014/0018923 A1    Jan. 16, 2014

Related U.S. Application Data

(63) Continuation of application No. 13/079,142, filed on Apr. 4, 2011, now Pat. No. 8,540,721.

(51) Int. Cl.
| | |
|---|---|
| *A61B 17/70* | (2006.01) |
| *A61B 17/02* | (2006.01) |
| *A61F 2/44* | (2006.01) |
| *A61F 2/46* | (2006.01) |

(52) U.S. Cl.
CPC ............... *A61F 2/44* (2013.01); *A61B 17/025* (2013.01); *A61F 2002/4687* (2013.01); *A61B 2017/0256* (2013.01); *A61F 2002/4624* (2013.01); *A61F 2/4611* (2013.01); *A61F 2002/4697* (2013.01); *A61F 2002/4627* (2013.01)
USPC ...................................................... 606/86 A

(58) Field of Classification Search
USPC .......... 606/246, 86 R, 102, 86 A, 99, 90, 105, 606/279; 623/17.11, 17.15, 17.16
See application file for complete search history.

(56) References Cited

U.S. PATENT DOCUMENTS

| | | | |
|---|---|---|---|
| 3,486,505 | A | 12/1969 | Morrison |
| 3,762,400 | A | 10/1973 | McDonald |
| 4,714,469 | A | 12/1987 | Kenna |
| 5,122,130 | A | 6/1992 | Keller |
| 5,431,658 | A | 7/1995 | Moskovich |
| 5,571,109 | A | 11/1996 | Bertagnoli |

(Continued)

FOREIGN PATENT DOCUMENTS

| | | |
|---|---|---|
| EP | 0637439 A1 | 2/1995 |
| EP | 1295578 A2 | 3/2003 |

(Continued)

OTHER PUBLICATIONS

Synthes, Inc. "Luminary AUF. Disc preparation and implant insertion instruments" pp. 1-23, 2006.

(Continued)

*Primary Examiner* — Pedro Philogene
*Assistant Examiner* — David Comstock
(74) *Attorney, Agent, or Firm* — Matthew B. Dernier, Esq.; Gibson & Dernier LLP

(57) ABSTRACT

Methods and apparatus for inserting an implant into an intervertebral cavity between adjacent vertebral bodies provide for: adjust an initial height between inner surfaces of respective first and second ramps of an inserter; simultaneously sliding first and second ramps of the inserter, and the implant, proximally, toward distal ends of the first and second ramps, such that the vertebral contact surfaces of the respective first and second ramps separate and distract the vertebral bodies and receive the implant into the intervertebral space with no compressive loading, while holding an initial angle between the ramps substantially constant.

21 Claims, 12 Drawing Sheets

(56) References Cited

U.S. PATENT DOCUMENTS

| | | |
|---|---|---|
| 5,599,279 A | 2/1997 | Slotman et al. |
| 5,683,399 A | 11/1997 | Jones |
| 6,159,215 A | 12/2000 | Urbahns |
| 6,478,800 B1 | 11/2002 | Fraser et al. |
| 6,569,168 B2 | 5/2003 | Lin |
| 6,616,671 B2 | 9/2003 | Landry et al. |
| 6,652,533 B2 | 11/2003 | O'Neil |
| 6,755,841 B2 | 6/2004 | Fraser et al. |
| 6,770,074 B2 | 8/2004 | Michelson |
| 6,824,565 B2 | 11/2004 | Muhanna et al. |
| 6,887,248 B2 | 5/2005 | McKinley |
| 6,986,772 B2 | 1/2006 | Michelson |
| 7,070,598 B2 | 7/2006 | Lim |
| 7,087,055 B2 | 8/2006 | Lim et al. |
| 7,204,852 B2 | 4/2007 | Marnay |
| 7,294,134 B2 | 11/2007 | Weber |
| 7,608,078 B2 | 10/2009 | Berry |
| 7,625,377 B2 | 12/2009 | Veldhuizen |
| 7,625,379 B2 | 12/2009 | Puno et al. |
| 7,896,884 B2 | 3/2011 | Wing et al. |
| 2002/0116009 A1 | 8/2002 | Fraser et al. |
| 2003/0055434 A1 | 3/2003 | O'Neil |
| 2004/0030346 A1 | 2/2004 | Frey |
| 2004/0066884 A1 | 4/2004 | Hermann Claus et al. |
| 2004/0225295 A1 | 11/2004 | Zubok |
| 2004/0267277 A1 | 12/2004 | Zannis et al. |
| 2005/0021042 A1 | 1/2005 | Marnay et al. |
| 2005/0113842 A1 | 5/2005 | Bertagnoli et al. |
| 2005/0143747 A1 | 6/2005 | Zubok et al. |
| 2005/0165408 A1 | 7/2005 | Puno et al. |
| 2005/0182416 A1 | 8/2005 | Lim et al. |
| 2006/0030856 A1 | 2/2006 | Drewry et al. |
| 2006/0030857 A1 | 2/2006 | de Villiers |
| 2006/0052793 A1 | 3/2006 | Heinz |
| 2006/0122701 A1 | 6/2006 | Kiester |
| 2006/0241641 A1 | 10/2006 | Albans |
| 2006/0241643 A1 | 10/2006 | Lim et al. |
| 2007/0016220 A1 | 1/2007 | Michelson |
| 2007/0191857 A1 | 8/2007 | Allard et al. |
| 2008/0161817 A1 | 7/2008 | Parsons et al. |
| 2010/0069914 A1 | 3/2010 | Puno et al. |
| 2010/0249792 A1 | 9/2010 | Bonvallet et al. |

FOREIGN PATENT DOCUMENTS

| | | |
|---|---|---|
| EP | 1323396 A2 | 7/2003 |
| WO | 2004066884 A1 | 8/2004 |
| WO | 2005072662 A1 | 8/2005 |
| WO | 2007055819 A2 | 5/2007 |
| WO | 2008021645 A2 | 2/2008 |
| WO | 2009014640 A1 | 1/2009 |
| WO | 2009023157 A1 | 2/2009 |

OTHER PUBLICATIONS

Related U.S. Appl. No. 11/622,545, filed Jan. 12, 2007.
European search report for corresponding EP application 12075037.7, dated Aug. 20, 2012.

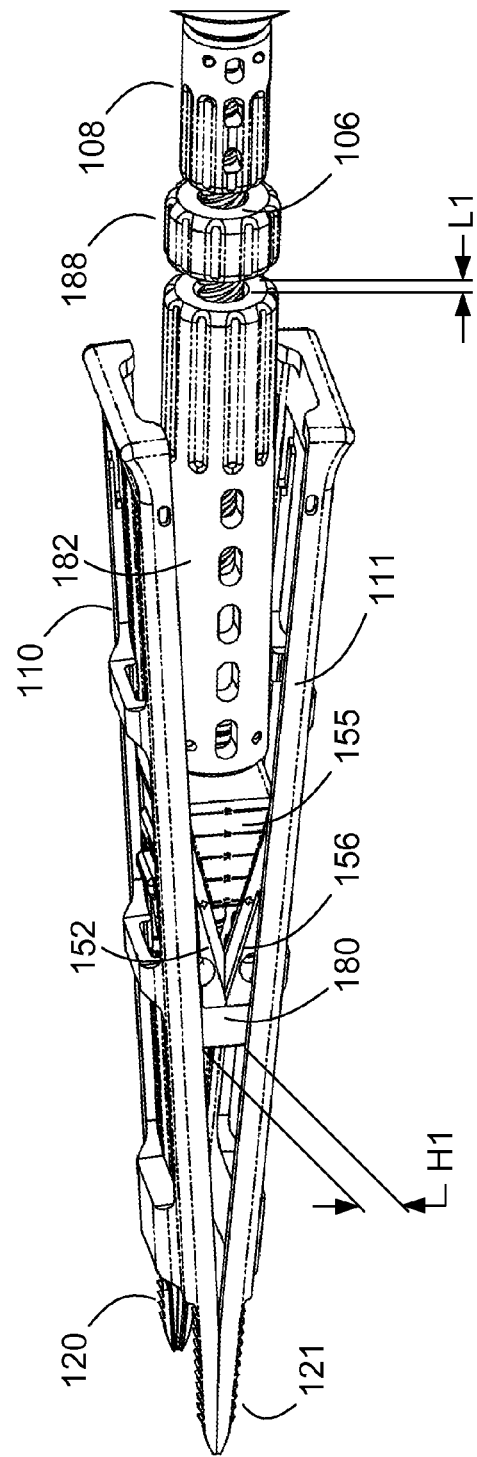

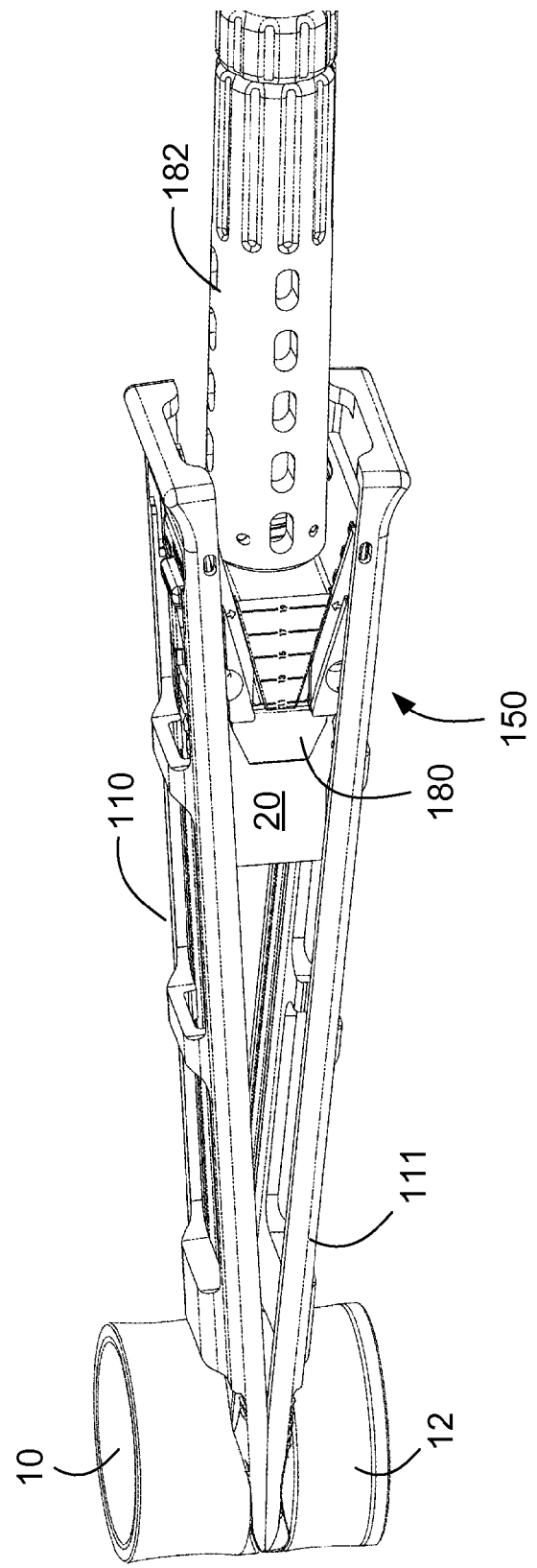

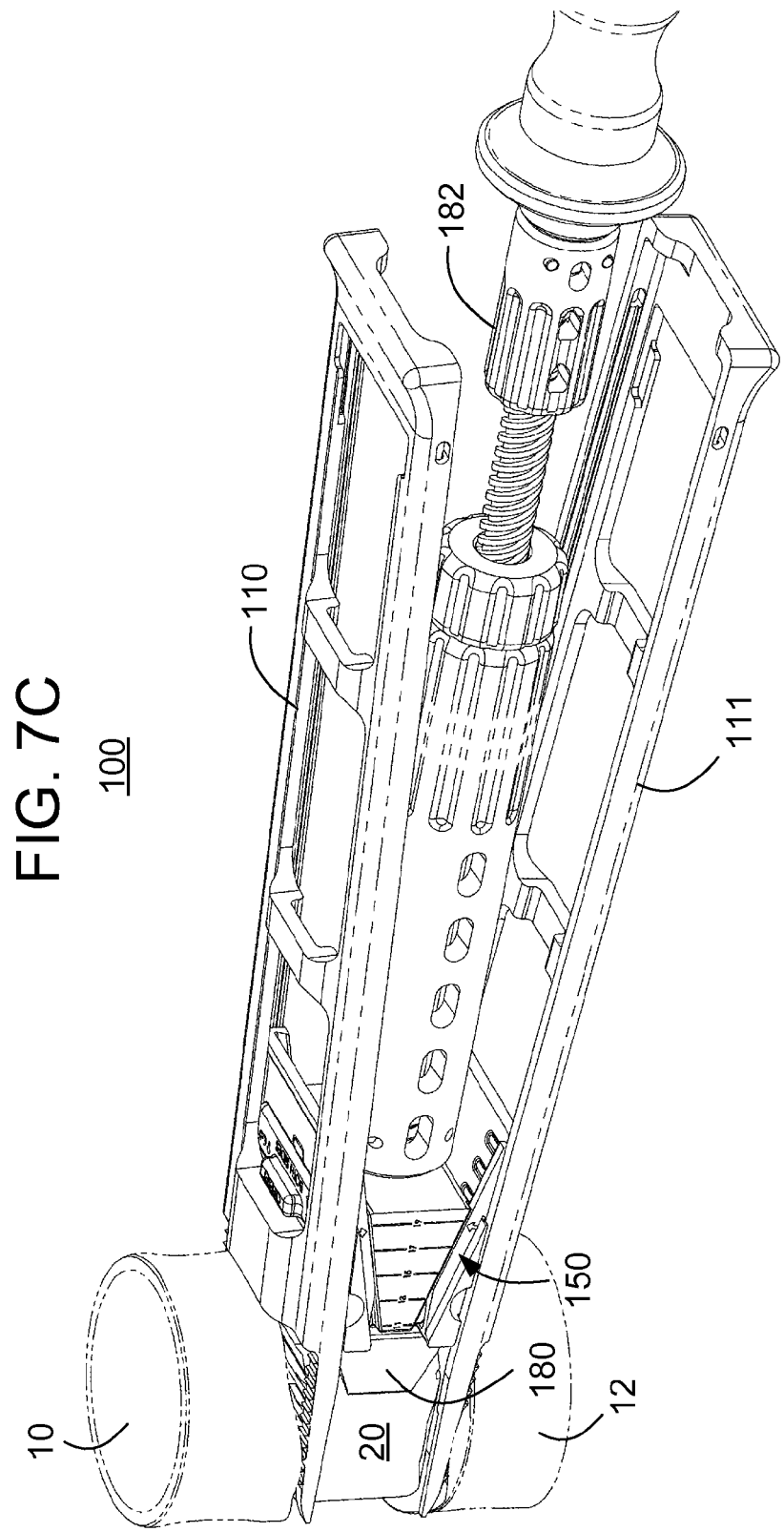

ADJUSTABLE APPARATUS AND METHODS FOR INSERTING AN IMPLANT

CROSS REFERENCE TO RELATED APPLICATIONS

This is a continuation application, which claims priority to U.S. Ser. No. 13/079,142, filed Apr. 4, 2011, entitled ADJUSTABLE APPARATUS AND METHODS FOR INSERTING AN IMPLANT, the entire disclosure of which is hereby incorporated by reference.

BACKGROUND

Embodiments of the present invention are directed to methods and apparatus for interbody distraction and implant/transplant insertion.

Intervertebral devices (commonly known as interbody spacers, and allograft transplants) have been developed for use in the reconstruction of collapsed inter-vertebral and/or otherwise damaged disc spaces. Herein, a gap separating two adjacent bodies may be referred to as an interbody cavity. A gap separating two adjacent vertebral bodies may be referred to as an intervertebral cavity or space.

In some procedures, surgeons insert these intervertebral devices into the intervertebral space of a patient's spine to facilitate bone fusion between and into the contiguous involved vertebrae. This fusion creates a new solid bone mass, which acts to hold the spinal segment at an appropriate biomechanically restored height as well as to stop motion in a painful segment of the spine. Intervertebral devices surgically placed in such involved interbody regions can thus stimulate interbody bone in-growth such that the operated anterior spinal segments heal into a contiguous bone mass, i.e., fusion occurs.

Additionally and/or alternatively, surgeons use intervertebral devices (and/or biological alternatives) to provide weight bearing support between adjacent vertebral bodies, and thereby correct or alleviate a variety of clinical problems. In this regard, surgeons use intervertebral devices for surgical therapy for degenerative disc disease (DDD), discogenic low back pain, spondylolisthesis, and/or reconstruction following tumor or infection surgery, and other spine related maladies requiring surgical intervention.

In many implant designs, a relatively hard or sturdy implant construct is formed from a selected biocompatible material such as metal, ceramic, or carbon fiber-reinforced polymer. This implant construct often has a partially open or porous configuration and is coated or partially filled with a selected bone ingrowth-enhancing substance, such as harvested bone graft supplied from the patient, human donor allograft bone transplant material supplied by a tissue bank, genetically cultivated bone growing protein substitutes, and/or other biological/biochemical bone extenders. Such devices, when implanted into the intervertebral space, promote ingrowth of blood supply and grow active and live bone from the adjacent spinal vertebrae to inter-knit with the implant, thereby eventually immobilizing or fusing the adjacent spinal vertebrae. Such implants also commonly include a patterned exterior surface such as a ribbed or serrated surface, or screw thread geometry, to achieve enhanced mechanical locking with the adjacent vertebrae during the bone ingrowth/fusion process.

The inventory of available intervertebral devices has expanded to include machined, transplantable allograft bone spacers. Bone Banks and tissue processors are able to precision-engineer donated human bone to specific vertebral interbody milled dimensions most likely to fit into the affected intra-discal zones. For many surgeons, these biological devices may provide a better option for a particular patient than the use of man-made materials.

The intervertebral or interbody implants of these general types have achieved a significant degree of clinical success. Notwithstanding this success, a variety of problems arise in connection with surgical interbody implant placement. Surgeons can have difficulty with the implantation process because of individual pathology, deformity, anatomical space restraints, or implant material limitations. Often, implant placement proves a difficult and time-consuming procedure when the soft tissue of the support elements of the adjacent vertebrae degenerate, causing collapse of the spaces between the vertebrae. This degenerative condition, coupled with compromised adjacent tissues, nerves and vasculature, may impede physical and visual access to the intervertebral space.

Spine surgery of this type may require removal of the remaining disc material, release of the contracted soft tissues around the intervertebral disc space, and some degree of distraction or pulling apart of the adjacent vertebrae in an attempt to restore disc space height, realign the spine, and indirectly decompress the nerve roots exiting the spine posteriorly at the affected level. This distraction procedure has traditionally required the use of several surgical distraction instruments, which may increase the overall complexity of the procedure, intensify the invasiveness of the surgical procedure, and possibly lead to iatrogenic vascular and neurosurgical injuries which can cause intraoperative surgical complications. At the same time, use of multiple instruments may limit the surgeon's manual access and clear view of the involved intervertebral space.

After the surgeon removes the disc material, a clean aperture should remain in which to place the intervertebral implant device. Typically, the surgeon grasps the device with a special pliers-like tool and places it at the mouth of the aperture. Then the surgeon typically uses extreme force as he or she hammers on the tool so that the implant device achieves its final placement. This hammering technique applies enormous shear forces through the implant device. As the implants have material and engineering limitations, such forces may cause the implant to fracture, shear, or break apart as a result of the forceful insertion. In addition, some implant designs require materials which do not tolerate the use of impaction-type forces that are so often necessary to advance the implant into the intervertebral space.

A variety of intervertebral implant insertion instruments have been developed in recent years as a result of efforts to simplify surgical distraction of the intervertebral space, while facilitating placement of the implant therein. See, for example, U.S. Pat. Nos. 6,755,841; 6,478,800; and 6,652,533; and U.S. Publication No. 2005/0165408 which disclose instruments for advancing an intervertebral implant between a pair of pivotally mounted distraction levers used to engage and distract adjacent vertebral structures. In these designs, the advancing movement of the implant is accompanied by wedged separation of the distal end tips of the levers which are engaged with and thereby separate or distract the adjacent vertebral structures.

While such implant insertion instruments provide a significant improvement in the art, the implant is not always safeguarded against substantial and potentially undesirable compression and shear forces during such advancing displacement between the pivoting distraction levers. In addition, these instruments have not provided a simple mechanism for quickly and easily retracting the distal end tips of the levers from the distraction space following intervertebral placement of the implant. Moreover, these instruments have not provided the ability to accommodate implants of different sizes, such as implants having different height dimensions, which may be indicated by specific patient requirements, without altering the insertion angle of the distal end tips of the distraction levers. In this regard, an amplified increase in the tip insertion angle, associated with implantation of a significantly taller implant, can undesirably increase the complexity and difficulty of the surgical implantation procedure.

Further advancements in insertion instruments and procedures are disclosed in co-pending U.S. patent application Ser. No. 11/622,545, filed Jan. 12, 2007, the entire disclosure of which is hereby incorporated by reference. The instruments and procedures disclosed therein provide for insertion of an implant without requiring the hammering technique and resultant shear forces through the implant device. Instead, respective ramps (at a given angle with respect to one another) are inserted into the intervertebral disc space and vertebral distraction is carried out by separating the ramps while keeping the angle fixed. Once the vertebrae are distracted, the implant slides along the ramps into position without any loading and/or insertion forces. When the implant is in place, the ramps are moved towards one another (again maintaining the given angle), which gently applies the vertebral loading to the implant and permits removal of the ramps from the intervertebral space.

Although the insertion instruments and procedures of U.S. patent application Ser. No. 11/622,545 represent a significant advancement over the art, there is still room for improvement. There exists, therefore, a continuing need for improvements in and to intervertebral implant insertion instruments and related intervertebral implants for use therewith, particularly with respect to quickly and easily distracting the intervertebral space for facilitated placement of an implant having a range of different heights, for safeguarding the implant against compression and shear forces during intervertebral distraction and insertion.

SUMMARY OF THE INVENTION

According to one or more aspects of the present invention, an instrument for inserting an implant into a vertebral space may include: first and second ramps, each including: (i) opposing outer and inner surfaces, each extending between proximal and distal ends thereof, and (ii) a vertebral contact surface located at the distal end thereof and in opposing relation to the inner surface thereof; and first and second wedges, each including: (i) a base side oriented toward the inner surface of a respective one of the first and second ramps, and defining a reference plane, (ii) an incline side defining a sliding plane that is at an acute angle to the reference plane, and (iii) a wedge coupling element operating to slidingly engage the incline side of the other of the first and second wedges, such that the sliding planes of the first and second wedges slide parallel to one another, wherein at least one of the first and second wedges includes a ramp coupling element located proximate to the base side thereof and operating to slidingly engage a respective one of the first and second ramps such that the reference plane slides substantially parallel thereto.

The first and second wedges operate to establish an initial angle between the vertebral contact surfaces of the respective first and second ramps. Sliding the first and second wedges relative to one another along the sliding planes thereof operates to adjust an initial height between the inner surfaces of the respective first and second ramps. Simultaneous sliding advancement of the first and second wedges toward the distal ends of the first and second ramps, by way of the respective ramp coupling elements, separates the vertebral contact surfaces of the respective first and second ramps while holding the initial angle therebetween substantially constant.

A proximal-distal axis is defined by the proximal and distal ends of the first and second ramps; each of the sliding planes of the first and second wedges define a normal vector thereto; the normal vector of the sliding plane of one of the first and second wedges includes a component directed distally along the proximal-distal axis but no component directed proximally along the proximal-distal axis; and the normal vector of the sliding plane of the other of the first and second wedges includes a component directed proximally along the proximal-distal axis but no component directed distally along the proximal-distal axis. The reference planes, sliding planes, and acute angles of the first and second wedges are designed such that the initial angle between the vertebral contact surfaces of the first and second ramps is between about 0 and 45 degrees. For example, the initial angle between the vertebral contact surfaces of the first and second ramps may be about 11 degrees.

The wedge coupling elements include one or more tongue-and-groove couplings operating to complementarily engage one another such that the incline side of the first wedge slidingly engages the incline side of the second wedge and the sliding planes of the first and second wedges slide parallel to one another.

The ramp coupling element elements include one or more tongue-and-groove couplings operating to complementarily engage one another, such that the base side of the first wedge slidingly engages the first ramp, and the base side of the second wedge slidingly engages the second ramp.

One of the first and second wedges includes a bore extending therethrough in a direction substantially parallel to the proximal-distal axis. The instrument may further include: (i) a rod extending through, and slideable within, the bore; and (ii) a stop element disposed at a distal end of the rod and operating to prevent the other of the first and second wedges from moving along the proximal-distal axis with respect to the rod; an actuator operating to slide the one of the first and second wedges on the rod and along the proximal-distal axis, thereby causing the first and second wedges to move relative to one another along the sliding planes thereof, and to adjust the initial height of the first and second ramps. The stop element operates to permit the other of the first and second wedges to slide in a direction transverse to the proximal-distal axis in reaction to the actuator sliding the one of the first and second wedges on the rod along the proximal-distal axis.

The instrument may further include one or more tongue-and-groove couplings operating to slidingly connect the stop element and the other of the first and second wedges such that the stop element operates to permit the other of the first and second wedges to slide in the direction transverse to the proximal-distal axis in reaction to the one of the first and second wedges sliding on the rod along the proximal-distal axis. The one or more tongue-and-groove couplings operate to prevent the other of the first and second wedges from moving away from the stop element proximally or distally along the proximal-distal axis. For example, the actuator may include: a threaded portion of the rod; and a nut in threaded engagement with the threaded portion of the rod such that rotation of the nut advances an engagement element thereof to move the one of the first and second wedges on the rod and along the proximal-distal axis.

The instrument may further include calibration markings on at least one of the first and second wedges providing a calibrated visual indication of the relative movement of the first and second wedges and resultant adjustment of the initial height of the first and second ramps.

According to one or more aspects of the present invention, an instrument for inserting an implant into a vertebral space may include: first and second ramps, each including: (i) opposing outer and inner surfaces, each extending between proximal and distal ends thereof, and (ii) a vertebral contact surface located at the distal end thereof and in opposing relation to the inner surface thereof; first and second wedges, each including: (i) a base side oriented toward the inner surface of a respective one of the first and second ramps, and defining a reference plane, (ii) an incline side defining a sliding plane that is at a first acute angle to the reference plane, and (iii) a ramp coupling element located proximate to the base side and operating to slidingly engage a respective one of the first and second ramps such that the reference plane slides substantially parallel thereto; and a third wedge including: (i) first and second opposing incline sides, each defining a respective first and second sliding plane, which are at a second acute angle with respect to one another, (ii) first and second wedge coupling elements, each operating to slidingly engage a respective one of the incline sides of the first and second wedges, such that the first sliding plane of the third wedge slides parallel to the sliding plane of the first wedge, and such that the second sliding plane of the third wedge slides parallel to the sliding plane of the second wedge.

The first, second, and third wedges operate to establish an initial angle between the vertebral contact surfaces of the respective first and second ramps. Sliding the third wedge relative to the first and second wedges operates to adjust an initial height between the inner surfaces of the respective first and second ramps. Simultaneous sliding advancement of the first, second, and third wedges toward the distal ends of the first and second ramps, by way of the respective ramp coupling elements, separates the vertebral contact surfaces of the respective first and second ramps while holding the initial angle therebetween substantially constant.

The third wedge may include the bore extending therethrough in a direction substantially parallel to the proximal-distal axis. The instrument may further include: (i) the rod extending through, and slideable within, the bore; and (ii) the stop element disposed at a distal end of the rod and operating to prevent the first and second wedges from moving along the proximal-distal axis with respect to the rod. Thus, the actuator may operate to slide the third wedge on the rod and along the proximal-distal axis, thereby causing the third wedge to move relative to the first and second wedges along the sliding planes thereof, and to adjust the initial height of the first and second ramps. The stop element operates to permit the first and second wedges to slide in opposite directions transverse to the proximal-distal axis in reaction to the actuator sliding the third wedge on the rod along the proximal-distal axis.

The separation of the first and second ramps, while maintaining the initial angle therebetween substantially constant, operates to provide parallel distraction of adjacent bodies when the insertion instrument is positioned within an interbody cavity. The instrument is configured to receive a compressive force, imparted by vertebral bodies adjacent to the intervertebral space, on the first and second ramps, thereby avoiding loading the implant with the compressive force during insertion of the instrument into the intervertebral space. The instrument operates to discontinue receiving the compressive force imparted by the vertebral bodies once the implant insertion is complete, thereby transferring the compressive force to the implant.

According to one or more aspects of the present invention, a method for inserting an implant into an intervertebral cavity between adjacent vertebral bodies using one or more of the instruments discussed above includes one or more of: sliding the first and second wedges relative to one another (or in an alternative embodiment, the third wedge relative to the first and second wedges) along the sliding planes thereof to adjust an initial height between the inner surfaces of the respective first and second ramps; and determining that the initial height is sufficient to exceed a height of the implant such that no portion of the implant extends to or beyond the inner surfaces of the respective first and second ramps.

The method may further include one or more of: simultaneously sliding the first and second wedges (or the first, second and third wedges), and the implant, proximally, away from the distal ends of the first and second ramps, such that the vertebral contact surfaces of the respective first and second ramps advance toward one another while holding the initial angle therebetween substantially constant; and inserting the distal ends of the first and second ramps into the intervertebral space.

The method may further include one or more of: simultaneously sliding the first and second wedges (or the first, second and third wedges), and the implant, distally toward the distal ends of the first and second ramps, such that the vertebral contact surfaces of the respective first and second ramps separate from one another while holding the initial angle therebetween substantially constant; continuing the sliding such that the vertebral contact surfaces of the respective first and second ramps distract the respective vertebral bodies sufficiently to receive the implant into the intervertebral space without compressively loading the implant; and continuing the simultaneous sliding toward the distal ends of the first and second ramps, such that the implant is received into the intervertebral space without compressively loading the implant.

The method may further include one or more of: disengaging the implant from the first and second wedges; and simultaneously sliding the wedges, without the implant, proximally, away from the distal ends of the first and second ramps, such that the vertebral contact surfaces of the respective first and second ramps advance toward one another while holding the initial angle therebetween substantially constant; continuing the sliding such that the vertebral contact surfaces of the respective first and second ramps permit the vertebral bodies to compressively load the implant; and withdrawing the distal ends of the first and second ramps from the intervertebral space.

Other features and advantages of the present invention will become more apparent from the following detailed description, taken in conjunction with the accompanying drawings which illustrate, by way of example, the principles of the invention.

BRIEF DESCRIPTION OF THE DRAWINGS

For the purposes of illustration, there are forms shown in the drawings that are presently preferred, it being understood, however, that the invention is not limited to the precise arrangements and instrumentalities shown.

FIGS. 4A, 4B, 4C are side perspective views of the instrument of FIG. 1 in various stages of adjustment;

FIGS. 7A, 7B, 7C are side perspective views of the instrument of FIG. 1 in various stages of distraction and insertion of an implant into an intervertebral space.

DETAILED DESCRIPTION OF THE PREFERRED EMBODIMENTS

Figure 1:
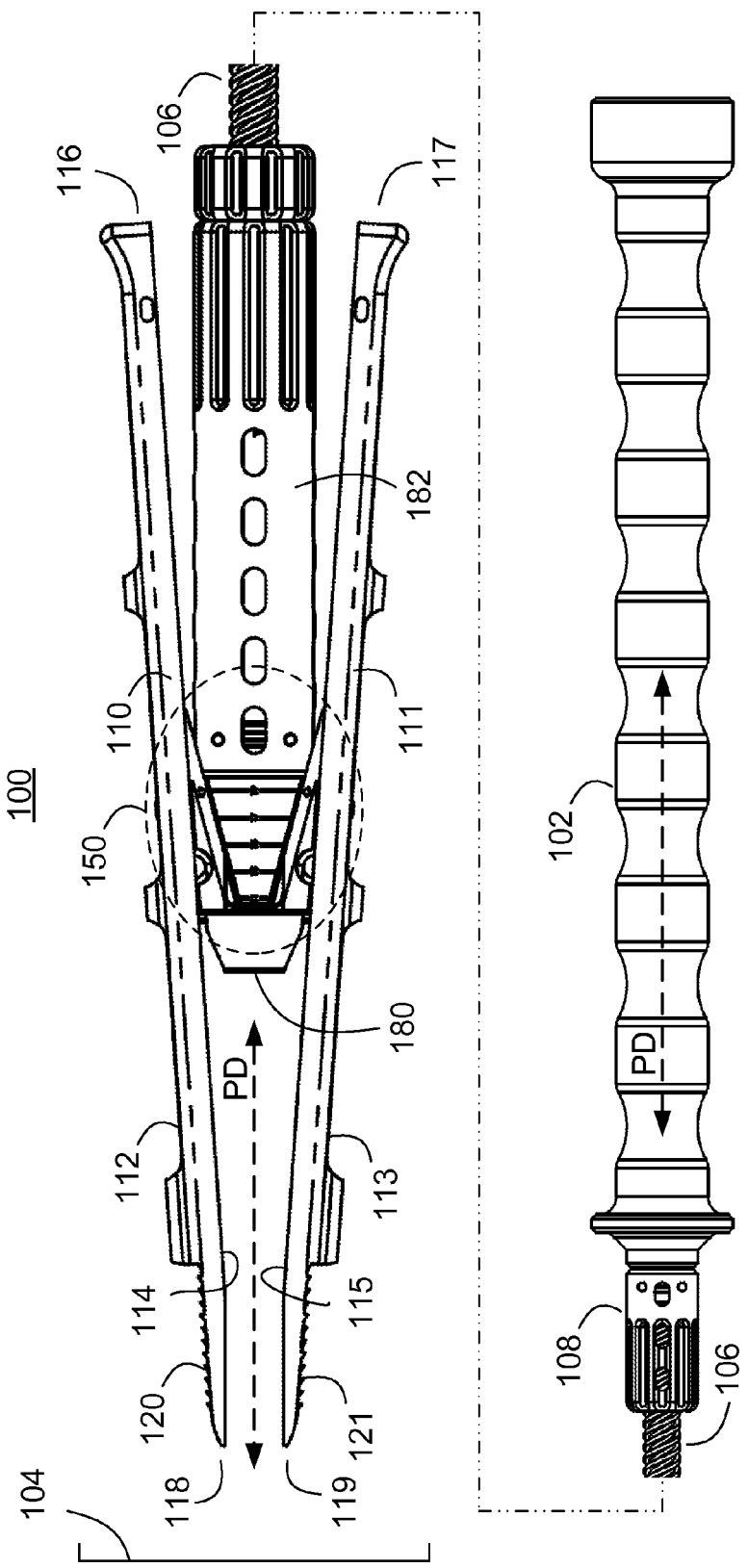
FIG. 1 is a side view of an intervertebral implant insertion instrument for use in distracting adjacent vertebrae and inserting an implant therebetween in accordance with one or more embodiments of the present invention.

FIG. 1 is a right-side, perspective view of an intervertebral implant insertion instrument 100 in accordance with one or more embodiments of the present invention. The insertion instrument 100 operates to distract adjacent bony structures, such as adjacent spinal vertebrae of a patient, and/or for inserting an implant (not shown, whether man-made, biological, and/or otherwise) therebetween. In one or more embodiments, the insertion instrument 100 and implant may be adapted for use in spinal surgical procedures for placement of the implant into a distracted intervertebral space wherein the implant may subsequently serve as a load bearing spacer element for maintaining a prescribed spacing between adjacent vertebral structures (or bodies).

In general, the instrument 100 may include a handle 102 at a proximal end thereof, and a distraction/insertion mechanism 104 at a distal end thereof. The handle 102 is coupled to the distraction/insertion mechanism 104 by way of a rod 106 and coupling 108. The handle 102 obviously provides the surgeon with means for controlling the orientation and movement of the instrument 100 during operative procedures. The distraction/insertion mechanism 104 provides numerous functionality, such as receiving an implant, distracting the vertebral bodies adjacent to the intervertebral space at issue, inserting the implant into the intervertebral space (notably without compressive loads on the implant), releasing the implant, and retracting the vertebral bodies to transfer compressive loads onto the implant.

The instrument 100 may include one or more ramps, preferably two ramps 110, 111 in an opposing configuration. More particularly, the first ramp 110 may include opposing outer and inner surfaces 112, 114, each extending between proximal and distal ends 116, 118 thereof. The first ramp 110 may further include a vertebral contact surface 120 located at the distal end 118 thereof, and in opposing relation to the inner surface 114 thereof. Although numerous alternatives exist, the second ramp 111 may be similar to, but oriented in as a mirror image of, the first ramp 110. Thus, the second ramp 111 may include opposing outer and inner surfaces 113, 115, each extending between proximal and distal ends 117, 119 thereof. The second ramp 111 may further include a vertebral contact surface 121 located at the distal end 119 thereof, and in opposing relation to the inner surface 115 thereof.

Figure 2:
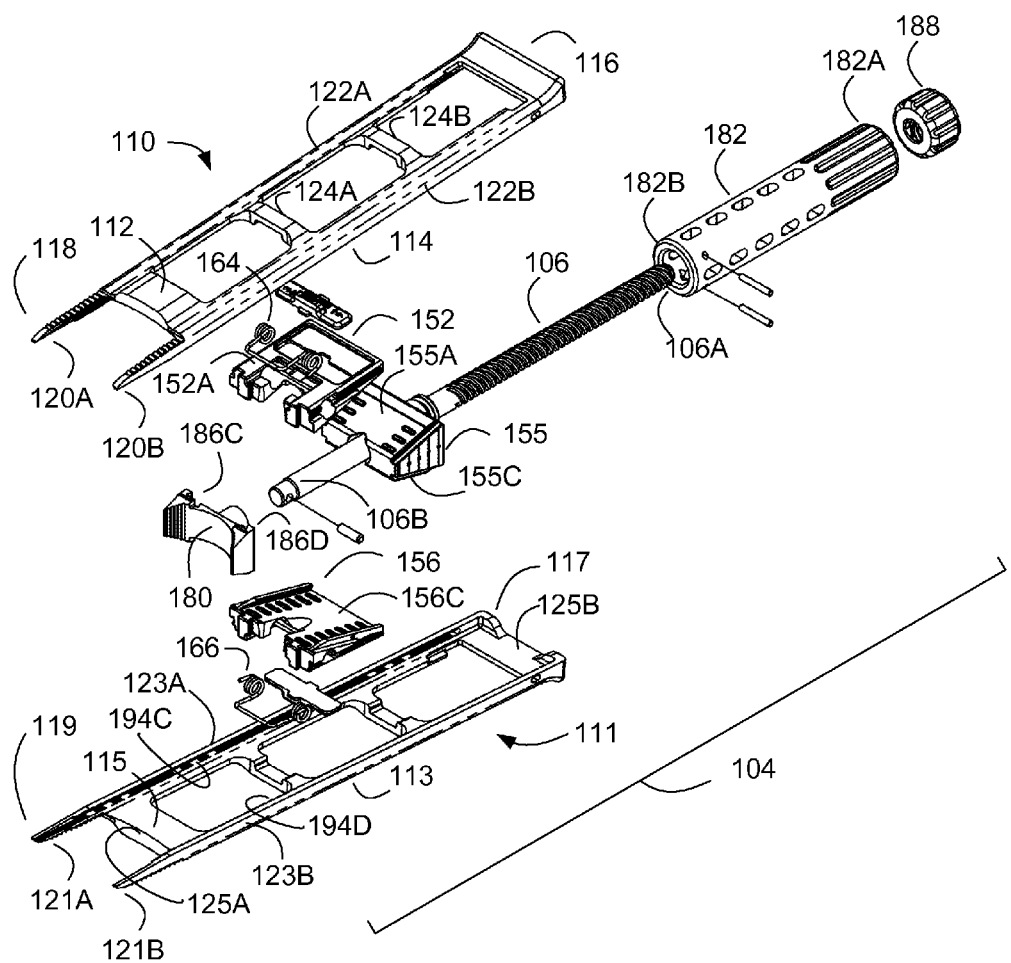
FIG. 2 is an exploded view of a portion of the instrument of FIG. 1.

With reference to FIG. 2, which is an exploded view of the distraction/insertion mechanism 104, the first ramp 110 may be implemented in any number of ways. For example, in the embodiment illustrated, the ramp 110 includes a pair of longitudinally extending portions 122A, 122B, oriented from the proximal end 116 to the distal end 118, and a plurality of laterally extending portions 124A, 124B, etc., oriented in a transverse relationship to the longitudinal portions 122. The respective opposing sides of the portions 122, 124 establish the outer and inner surfaces 112, 114, respectively. By way of example, the vertebral contact surface 120 may be implemented with a forked arrangement, including respective arms 120A, 120B extending distally at the distal end 118 of the first ramp 110. As discussed above, the second ramp 111 may be a mirror image of the first ramp 110. Thus, the ramp 111 may include longitudinally extending portions 123A, 123B, a plurality of laterally extending portions 125A, 125B, etc., and respective arms 121A, 121B at the distal end 119 of the second ramp 111.

Turning again to FIG. 1, the orientations of the first and second ramps 110, 111 generally define a proximal-distal (PD) axis. Although the specific relationships between the direction of the PD axis and each of the ramps 110, 111 are somewhat arbitrary, it is preferred that the PD axis is generally parallel to each of the ramps 110, 111. For example, in embodiments in which the ramps 110, 111 are not exactly parallel, such as the embodiment illustrated, however, the PD axis may not be exactly parallel to both, or either, of the ramps 110, 111. As illustrated, the PD axis is substantially (but not exactly) parallel to both ramps 110, 111, but is exactly parallel to an axis of the rod 106 and the handle 102. A skilled artisan, having read the entire disclosure, will appreciate that other definitions of the PD axis are possible without departing from the scope of the claimed invention.

The instrument 100 may further include a (ramp adjustment) assembly 150 located between the first and second ramps 110, 111 that operates to permit distance adjustments between the ramps 110, 111, as well as to permit distraction of the ramps 110, 111. In the present embodiment, the assembly 150 includes a number of wedge-shaped elements, and therefore may be referred to herein as a wedge assembly 150.

Figure 3A:
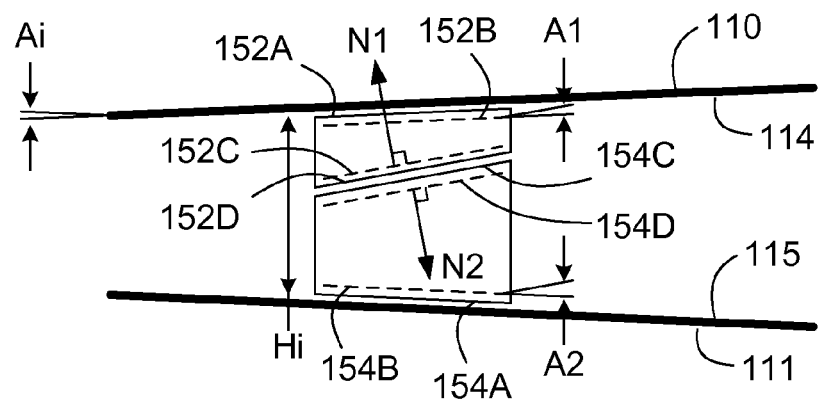
FIGS. 3A-3B are schematic, side views of alternative assemblies useful in implanting an adjustable wedge means for an intervertebral implant insertion instrument for use in distracting adjacent vertebrae and inserting an implant therebetween in accordance with one or more embodiments of the present invention.
Figure 3B:
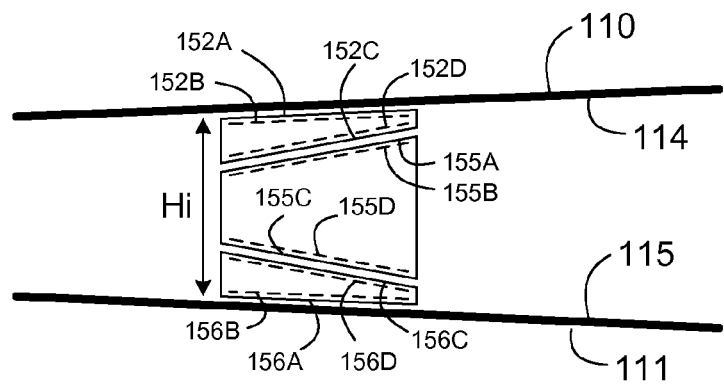

In general, the wedge assembly 150 operates to establish the orientation and movement of the ramps 110, 111 before, during, and after inserting the implant into the intervertebral space. With reference to FIGS. 3A-3B, which are simplified schematic diagrams, the wedge assembly 150 includes a plurality of wedges that operate to slide with respect to one another, and that slide relative to the first and second ramps 110, 111, to achieve certain desirable functionality. The implementation of the wedge assembly 150A illustrated in FIG. 3A employs two wedges, a first wedge 152 and a second wedge 154. The first wedge 152 includes a base side 152A oriented toward (and in this example slidingly engaging) the inner surface 114 of the first ramp 110. The base side 152A defines a reference plane 152B, which in this example is parallel to the base side 152A. The first wedge 152 also includes an incline side 152C, defining a sliding plane 152D (e.g., parallel to the incline side 152C) that is at an acute angle A1 to the reference plane 152B. The second wedge 154 includes a base side 154A oriented toward (and in this example slidingly engaging) the inner surface 115 of the second ramp 111. The base side 154A defines a reference plane 154B, which in this example is parallel to the base side 154A. The second wedge 154 also includes an incline side 154C, defining a sliding plane 154D (e.g., parallel to the incline side 154C) that is at an acute angle A2 to the reference plane 154B. The first and second wedges 152, 154 are slidingly coupled together at the respective incline sides 152C, 154C, such that the sliding planes 152D, 154D of the first and second wedges 152, 154 slide parallel to one another.

Further geometric details of the first and second wedges 152, 154 include the relationships of the respective sliding planes 152D, 154D and the PD axis. For example, each of the sliding planes 152D, 154D define a normal vector N1, N2. The normal vector N1 of the sliding plane 152D the first wedge 152 includes a component directed distally along the PD axis but no component directed proximally along the PD axis. Conversely, the normal vector N2 of the sliding plane 154D of the second wedge 154 includes a component directed proximally along the PD axis but no component directed distally along the PD axis. This relationship provides certain functionality, which will be discussed below.

As noted above, the first and second wedges 152, 154 operate to achieve certain desirable functionality. For example, the size, shape, and acute angles of the first and second wedges 152, 154 operate to establish an initial angle (Ai) between the vertebral contact surfaces 120, 121 of the respective first and second ramps 110, 111. By way of example, the initial angle may be between about 0 and 45 degrees, preferably about 11 degrees.

The size, shape, and acute angles of the first and second wedges 152, 154 may also operate to establish an initial height (H) between the respective first and second ramps 110, 111. Although the precise location at which the initial height (H) may be measured is somewhat arbitrary, one reasonable location is adjacent to, a just distal from, the wedge assembly 150. This is the location at which the insert will be disposed during insertion. Notably, sliding the first and second wedges 152, 154 relative to one another along the sliding planes 152D, 154D thereof, operates to adjust the initial height (H). Advantageously, the instrument 100 is operable to accommodate implants of differing heights by adjusting the initial height (H). Further discussion of the initial height (H) and its adjustment will be presented later in this specification.

Further, simultaneous sliding advancement of the first and second wedges 152, 154 toward the distal ends 118, 119 of the first and second ramps 110, 111, by way of the sliding engagement of the respective base sides 152A, 154A with the inner surfaces 114, 115 of the respective ramps 110, 111, separates the vertebral contact surfaces 120, 121 of the respective first and second ramps 110, 111, while holding the initial angle (Ai) therebetween substantially constant. Further details concerning this functionality and the advantages thereof will be presented later in this specification.

The implementation of the wedge assembly 150B illustrated in FIG. 3B also achieves the desirable functionality discussed above. As compared with assembly 150A, it is believed that the implementation of assembly 150B results in smoother mechanical motion and requires lower stresses in certain mechanical parts to achieve the requisite sliding motions. More specifically, the assembly 150B employs three wedges: a first wedge 152, a second wedge 156, and a third wedge 155. In all significant respects, the first wedge 152 may be the same as the wedge 152 discussed with respect to assembly 150A (FIG. 3A). The second wedge 156 is in an orientation that is a mirror image of (and opposing) the first wedge 152. Thus, the second wedge 156 includes a base side 156A oriented toward (and in this example slidingly engaging) the inner surface 115 of the second ramp 111. The base side 156A defines a reference plane 156B, which in this example is parallel to the base side 156A and parallel to the inner surface 115 of the second ramp 111. The second wedge 156 also includes an incline side 156C, defining a sliding plane 156D (e.g., parallel to the incline side 156C) that is at an acute angle to the reference plane 156B.

The third wedge 155 of the assembly 150B includes a first incline side 155A defining a respective first sliding plane 155B, and a second incline side 155C defining a respective second sliding plane 155D. The first and second incline sides 155A, 155C are preferably in opposing and mirror image orientations. The first and second sliding planes 155B, 155D are at an acute angle with respect to one another. When the above details are taken into consideration, it is preferred, in this example, that the third wedge 155 is of a generally symmetrical construction.

The first and third wedges 152, 155 are slidingly coupled together at the respective incline sides 152C, 155A, such that the sliding planes 152D, 155B of the first and third wedges 152, 155 slide parallel to one another. Similarly, the second and third wedges 156, 155 are slidingly coupled together at the respective incline sides 156C, 155C, such that the sliding planes 156D, 155D of the second and third wedges 156, 155 slide parallel to one another.

The functionality of the assembly 150B is similar to that of assembly 150A, with notable differences in the mechanisms that achieve the desired function. For example, the size, shape, and acute angles of the first, second, and third wedges 152, 156, 155 operate to establish the initial angle (Ai) between the vertebral contact surfaces 120, 121 of the respective first and second ramps 110, 111. Again, the initial angle (Ai) may be between about 0 and 45 degrees, preferably about 11 degrees. The size, shape, and acute angles of the first, second, and third wedges 152, 156, 155 may also operate to establish the initial height (H) between the respective first and second ramps 110, 111. Notably, sliding the third wedge 155 relative to the first and second wedges 152, 156 along the respective pairs of sliding planes 152D, 155B and 156D, 155D, operates to adjust the initial height (H). Further, simultaneous sliding advancement of first, second, and third wedges 152, 156, 155 toward the distal ends 118, 119 of the first and second ramps 110, 111, by way of the sliding engagement of the respective base sides 152A, 156A with the inner surfaces 114, 115 of the respective ramps 110, 111, separates the vertebral contact surfaces 120, 121 of the respective first and second ramps 110, 111, while holding the initial angle (Ai) therebetween substantially constant.

Figure 4B:
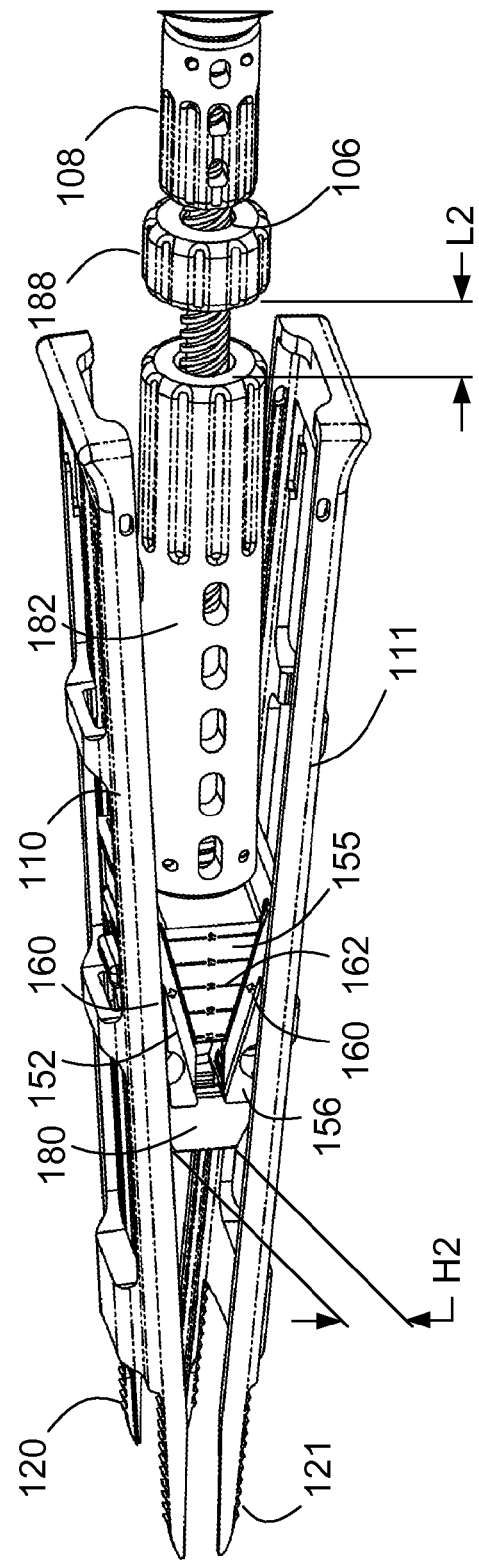

With reference to FIGS. 1 and 4A-4C, the instrument 100 employs the three-wedge configuration of assembly 150B (FIG. 3B), although skilled artisans will appreciate that the two-wedge configuration (or other numbers of wedges) may be employed in the alternative. A receptacle 180 is located adjacent and distal to the wedge assembly 150, and operates to detachably engage the implant (not shown) during the surgical insertion procedure. FIG. 4A illustrates the instrument 100 with the third wedge 155 in a particular position relative to the first and second wedges 152, 156. In this orientation, the first and second wedges 152, 156 are in opposing, mirror image, orientations with distal ends thereof in abutment with the receptacle 180. The respective pairs of sliding planes 152D, 155B and 156D, 155D (reference numbers omitted in FIGS. 4A-4C for clarity) of the wedges have been slid such that the third wedge 155 is more proximally disposed relative to the first and second wedges 152, 156. This particular orientation of the assembly 150 results in a particular initial height H1 (as measured just distal to the receptacle 180). In this example, and at this orientation, the dimensions of the relevant components of the instrument 100 result in: (1) the particular initial height H1; (2) the distal ends 118, 119 of the ramps 100, 111 just touching; and (3) a minimal distance between the vertebral contact surfaces 120, 121.

Among the advantages of setting the initial height to the level of H1 is to ensure that the overall height of the implant (specifically the dimension that extends between the ramps 110, 111) is below the distance between the inner surfaces 114, 115 of the ramps 110, 111, respectively. As will be discussed in more detail later in this specification, under such circumstances, the surgeon may ensure that the implant may move into the intervertebral space without experiencing any significant sheer forces or other compressive forces, as is common using many prior art techniques. Of course, if the height of the implant would extend beyond one or both of the outer surfaces 112, 113 of the ramps 110, 111, then the initial height H1 may not be sufficient and a different initial height should be considered.

With reference to FIG. 4B, sliding the third wedge 155, distally relative to the first and second wedges 152, 156, along the respective pairs of sliding planes 152D, 155B and 156D, 155D, operates to adjust the initial height from H1 to H2. In this orientation, the assembly 150 of the instrument 100, the first and second wedges 152, 156 are again in opposing, mirror image, orientations with distal ends thereof in abutment with the receptacle 180. As compared with the orientation of FIG. 4A, the first and second wedges 152, 156 and the receptacle 180 have not moved. The respective pairs of sliding planes 152D, 155B and 156D, 155D of the wedges have been slid such that the third wedge 155 is more distally disposed relative to the first and second wedges 152, 156 as compared with the orientation of FIG. 4A. The sliding of the third wedge 155 relative to the others results in a smooth change in the initial height from H1 to H2. In this example, and at this orientation, the dimensions of the relevant components of the instrument 100 result in: (1) the particular initial height H2; (2) the distal ends 118, 119 of the ramps 100, 111 having opened; and (3) a greater distance between the vertebral contact surfaces 120, 121 as compared with the orientation of FIG. 4A.

Again, at an initial height of H2, the overall height of the implant may be at or below the distance between the outer surfaces 112, 113 of the ramps 110, 111, respectively. If, however, the height of the implant would extend beyond one or both of the outer surfaces 112, 113 of the ramps 110, 111, then the initial height H2 may not be sufficient and further consideration should be given to a different initial height.

Figure 4C:
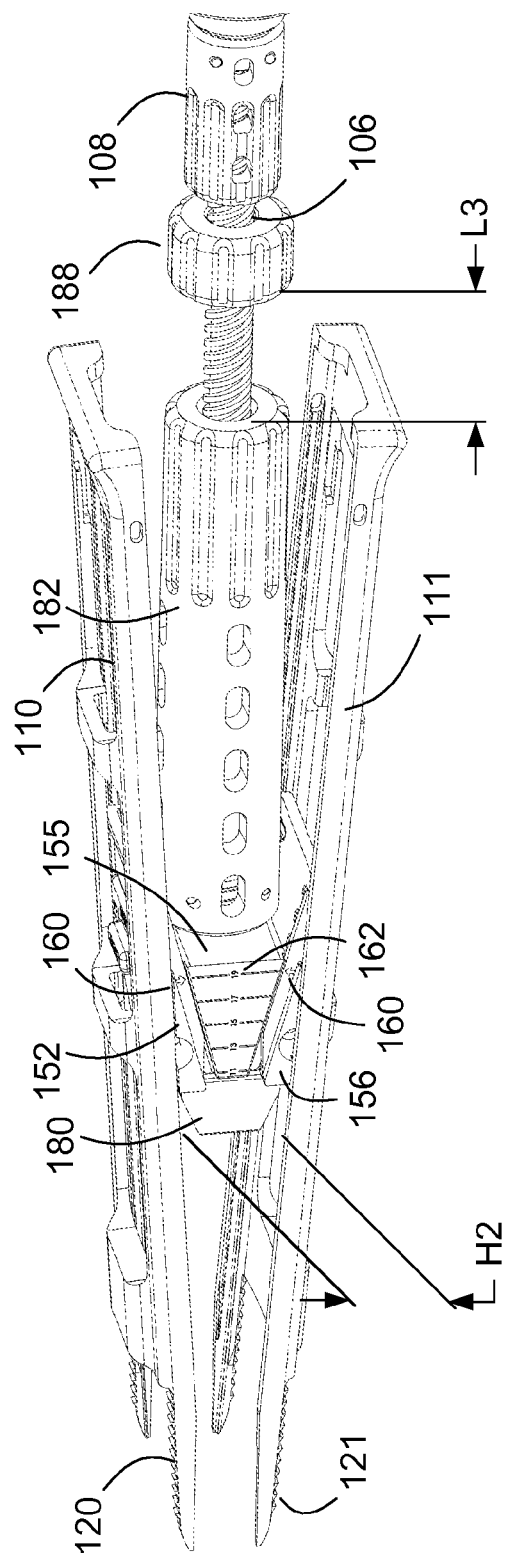

With reference to FIG. 4C, sliding the third wedge 155, even further distally relative to the first and second wedges 152, 156, along the respective pairs of sliding planes 152D, 155B and 156D, 155D, operates to adjust the initial height from H2 to H3. The respective pairs of sliding planes 152D, 155B and 156D, 155D of the wedges have been slid such that the third wedge 155 is more distally disposed relative to the first and second wedges 152, 156 as compared with the orientation of FIG. 4B. The sliding of the third wedge 155 relative to the others results in a smooth change in the initial height from H2 to H3, and a greater distance between the vertebral contact surfaces 120, 121.

With reference to FIG. 2 and FIGS. 4A-4C, the instrument 100 may include an actuator 182 operating to slide the third wedge 155 (preferably parallel or along the PD axis) relative to the first and second wedges 152, 156, thereby causing the wedges to move relative to one another along the respective pairs of sliding planes 152D, 155B and 156D, 155D, and to adjust the initial height H of the first and second ramps 110, 111.

In this embodiment, the actuator 182 is movable parallel to (or along) the PD axis by way of movable engagement along the rod 106. One of the wedges, such as the third wedge 155 includes a bore 184 extending therethrough in a direction substantially parallel to the PD axis. The rod 106 extends through, and is slidable within, the bore 182. An engagement element 182B at a distal end of the actuator 182 is coupled to a mating element 184A disposed at a proximal side of the third wedge 155. The rod 106 extends from the actuator 182, through the mating element 184A, and through the bore 184.

A stop element is disposed at a distal end 106B of the rod 106. In this embodiment, the receptacle 180 may operate as the stop element, which may be fixed to the distal ends 106B of the rod 106 by way of any suitable means, such as via a pin. The stop element of the receptacle 180 operates to prevent the first and second wedges 152, 156 from moving along (or parallel) to the PD axis, which is along the rod 106. Thus, as the actuator 182 moves the third wedge 155 along the rod 106 (in either direction), the stop element 180 keeps the first and second wedges 152, 156 fixed along the rod 106 (at least with reference to the PD axis). This action causes the wedges to slide at the pairs of sliding planes 152D, 155B and 156D, 155D, and to adjust the initial height H of the first and second ramps 110, 111. The stop element 180, however, permits the first and second wedges 152, 156 to slide in directions transverse to the PD axis (and transverse to the longitudinal axis of the rod 106) in response to the actuator 182 sliding the third wedge 155 relative to the first and second wedges 152, 156. This action permits the ramps 110, 111 to spread or retract and achieve the differing initial heights H.

Although any number of implementations of the stop element 180 are available to the skilled artisan, one approach to achieving the aforementioned functionality is to employ so-called tongue-and-groove structures. For example, with reference to FIGS. 2 and 6A-6B, the first wedge 152 may include one or more tongue structures 186A, 186B and the stop element 180 may include one or more corresponding groove structures 186C, 186D. In a preferred embodiment, the tongue-and-groove structures 186A, 186B, 186C, 186D may be in the form of dovetail shapes such that movement in directions parallel to the PD axis (along the rod 106) are prevented, yet transverse movement thereto is permitted. Skilled artisans will understand that alternatives in the positions of one or more of the tongues 186A, 186B and one or more of the grooves 186C, 186D are available. For example, one or more of the tongues 186A, 186B may instead be placed on the stop element 180, so long as a corresponding one or more of the groove elements 186C, 186D are available on the first wedge 152. Similar structures may be employed on the second wedge 156.

Although any number of variations in the implementation of the actuator 182 is available to the skilled artisan, one approach is to employ a threaded bore (not shown) within the actuator 182, which threadingly engages a threaded portion of the rod 106. As the actuator 182 is turned one way of the other, it moves along the rod 106 and correspondingly moves the third wedge 155 on the rod 106 and along (parallel to) the PD axis. As illustrated in FIGS. 4A-4C, the threaded position of the actuator 182 along the rod 106 may be characterized by distance L1 (to achieve the initial height of H1), distance L2 (to achieve the initial height of H2), and distance L3 (to achieve the initial height of H3). A lock nut 188 may be employed to fix the position of the actuator 182 once it has been placed in a suitable position to achieve the desired initial height H.

Figure 5:
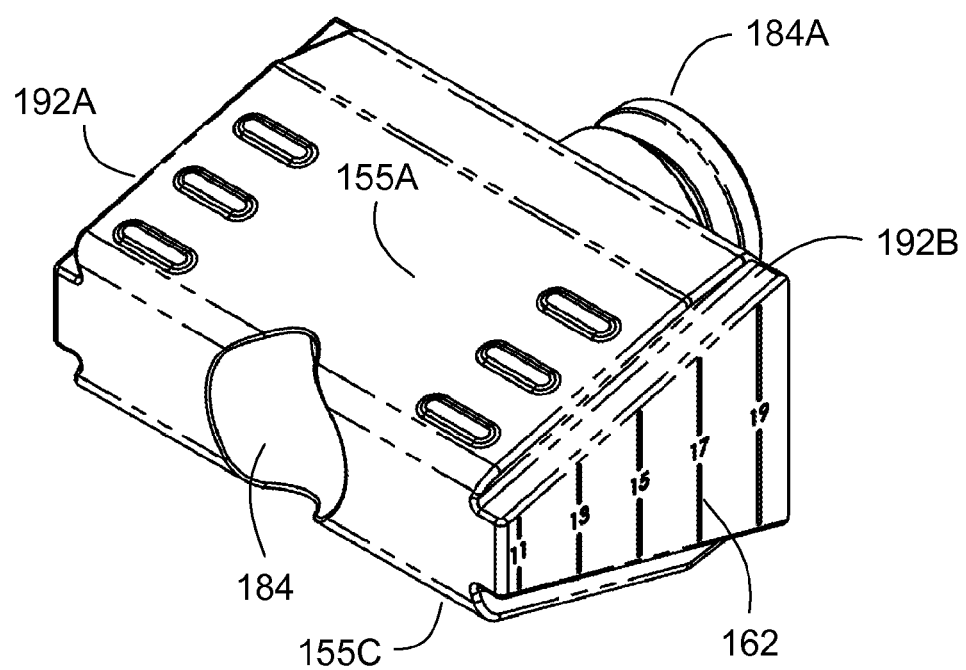
FIG. 5 is a perspective view of a wedge element suitable for use in the instrument illustrated in FIG. 1 and/or other embodiments disclosed and/or described herein.
Figure 6A:
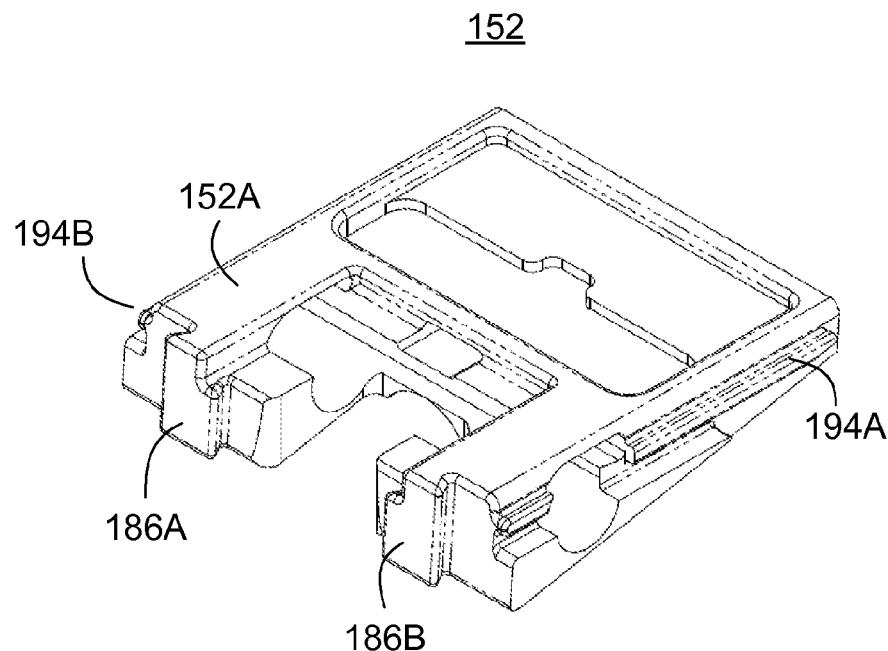
FIGS. 6A and 6B are perspective views of a further wedge element suitable for use in the instrument illustrated in FIG. 1 and/or other embodiments disclosed and/or described herein.
Figure 6B:
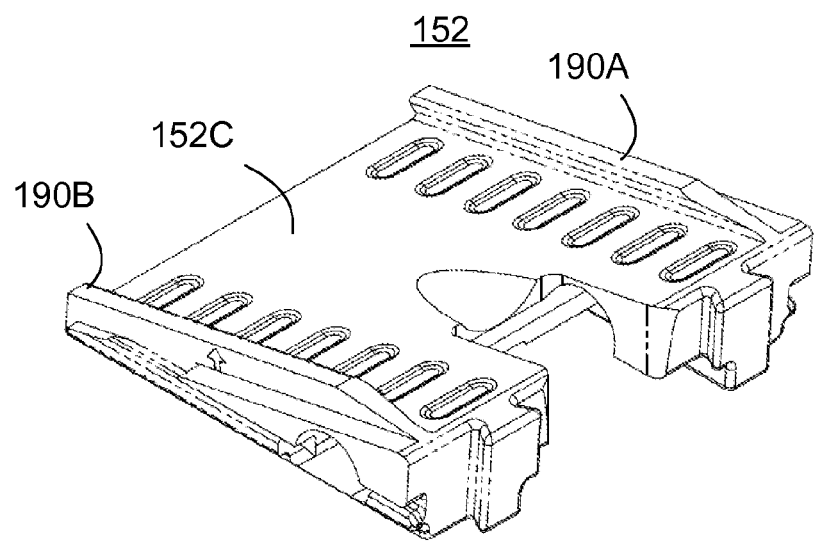

With reference to FIGS. 5, and 6B, the wedges 152, 156, 155 preferably include wedge coupling elements that operate to permit the incline sides of the respective wedges to remain in sliding orientation with one another. Although any number of variations in the implementation of the wedge coupling elements is available to the skilled artisan, one approach is to employ one or more tongue-and-groove couplings operating to complementarily engage one another such that the respective incline sides the respective wedges slidingly engage one another. For example, the first wedge 152 may include one or more tongue structures 190A, 190B and the third wedge 155 may include one or more corresponding groove structures 190C, 190D. Skilled artisans will understand that alternatives in the positions of one or more of the tongues 190A, 190B and one or more of the grooves 190C, 190D are available. For example, one or more of the tongues 190A, 190B may instead be placed on the third wedge 155, so long as a corresponding one or more of the groove elements 190C, 190D are available on the first wedge 152. Similar structures may be employed in connection with the wedge coupling between the second wedge 156 and the third wedge 155.

With reference to FIGS. 2, and 6A, the first and second wedges 152 156 preferably include ramp coupling elements disposed at the base side thereof that operate to permit the respective wedges to remain in sliding engagement with one of the respective ramps 110,111. Although any number of variations in the implementation of the ramp coupling elements is available to the skilled artisan, one approach is to employ one or more tongue-and-groove couplings operating to complementarily engage one another such that the respective base sides the respective wedges 152, 156 slidingly engage the respective ramps 110, 111. For example, the first wedge 152 may include one or more tongue structures 194A, 194B and the first ramp 110 may include one or more corresponding groove structures 194C, 194D. Given the orientation of the first ramp 110 in FIG. 2, the groove structures 194C, 194D cannot be seen in the illustration. As the second ramp 111 may be a mirror image of the first ramp 110, however, for the purposes of discussion, the groove structures 194C, 194D are shown on the second ramp 111. Skilled artisans will understand that alternatives in the positions of one or more of the tongues 194A, 194B and one or more of the grooves 194C, 194D are available. For example, one or more of the tongues 194A, 194B may instead be placed on the respective one of the ramps 110, 111, so long as a corresponding one or more of the groove elements 194C, 194D are available on the first wedge 152. Similar structures and alternatives may be employed in connection with the ramp coupling between the second wedge 156 and the second ramp 111.

In view of the foregoing, the instrument 100 provides the surgeon with flexibility to accommodate the insertion of implants of differing heights, without the need for exchanging/replacing some or all of the relevant components of the device. Instead, the surgeon can adjust the relative sliding position of the wedges 152, 156, 155 to achieve the desired initial height H. As best seen in FIGS. 4A-4C, the instrument 100 includes calibration markings 160, 162 on one or more of the wedges 152, 156, 155, thereby providing a calibrated visual indication of the relative movement of the third wedge 155 relative to the first and second wedges 152, 156, and the resultant adjustment of the initial height H of the first and second ramps 110, 111. More particularly, a reference marking 160 may be located on one or both of the first and second wedges 152, 156, and a corresponding reference marking 162 may be located on the third wedge 155. In this example, a series of markings 162 are provided to achieve the calibration function. When the relative positions of the markings 160, 162 are properly established, the alignment of the various markings 162 with the markings 160 may result in predetermined, calibrated initial heights.

Figure 7B:
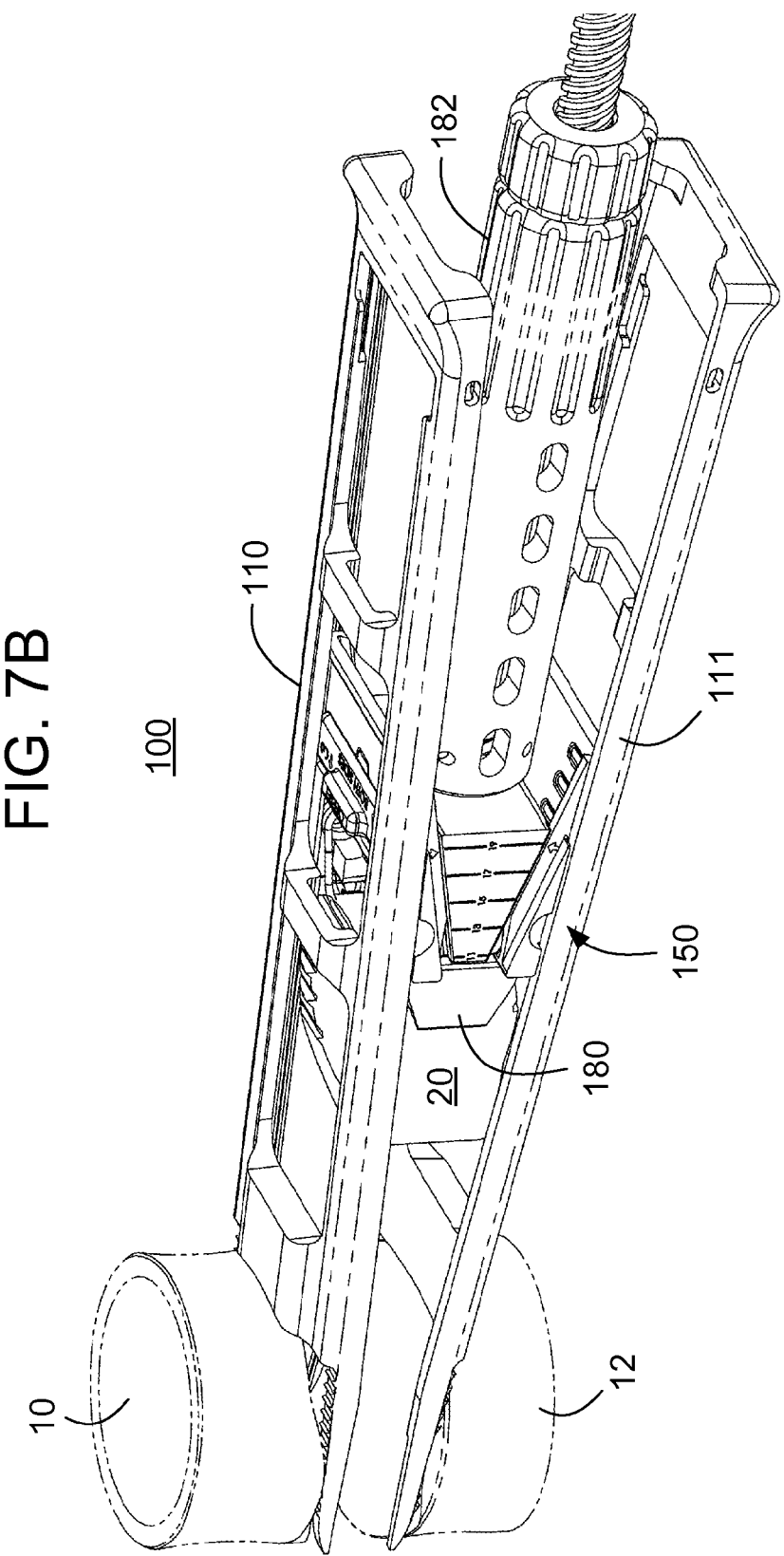

With reference to FIGS. 7A-7C, a method for inserting an implant 20 into an intervertebral cavity between adjacent vertebral bodies 10, 12 will now be described.

The implant 20 may be formed from a relatively sturdy and biocompatible material such as (but not limited to) a selected metal or metal alloy, bone, polymer, carbon fiber-reinforced polymer and/or ceramic. The implant 20 may be formed with a partially open or porous configuration and may be coated or partially filled with a selected bone ingrowth-enhancing substance, such as autogenous bone material harvested from the patient, with transplantable allogenic bone material supplied by a third party donor. Such devices, when implanted into the intervertebral space, may promote ingrowth of blood supply and live bone cells from the adjacent spinal vertebrae 10, 12 to inter-knit with the implant 20, thereby eventually immobilizing or fusing the adjacent spinal vertebrae 10, 12. Of course, alternative implants 20 are also contemplated, including those that preserve adjacent vertebral motion.

During the initial phases of the surgery, the remaining disc material between the vertebrae 10, 12 may be removed, and the contracted soft tissues around the intervertebral disc space may be released.

A height of the implant 20 is considered and adjustment of the initial height of the instrument 100 is adjusted. As previously discussed, the initial height Hi (preferably measured with reference to the relative positions of the first and second ramps 110, 111) is set to a level such that the overall height of the implant 20 (specifically the dimension that extends between the ramps 110, 111) is at or below the distance between the inner surfaces 114, 115 of the ramps 110, 111, respectively. This may be accomplished using, for example, a three-wedge assembly 150 (which was discussed in detail earlier in this specification). By way of example, the actuator 182 may be turned to slide the first and second wedges 152, 156 relative to one another along the sliding planes thereof, resulting in the adjustment of the initial height Hi between the inner surfaces 114, 115 of the respective first and second ramps 110, 111. The surgeon may make a determination that the initial height Hi is sufficient to exceed a height of the implant 20 such that no portion of the implant extends to or beyond the inner surfaces 114, 115 of the respective first and second ramps 110, 111.

Figure 8:
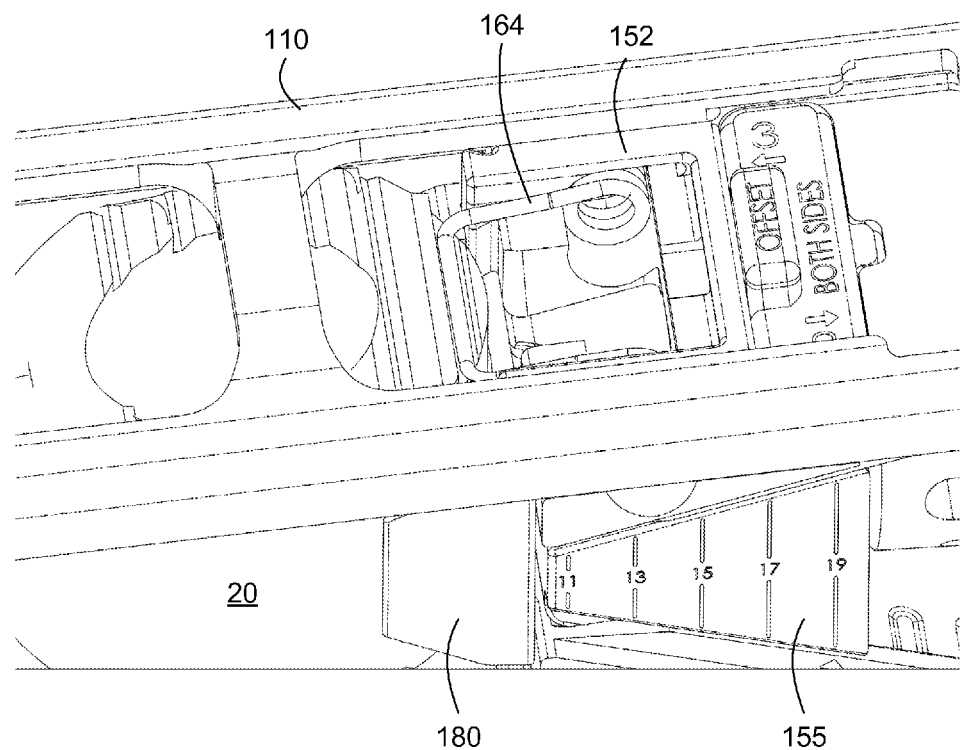
FIG. 8 is a perspective view showing details of the engagement of the implant and the instrument of FIG. 1.

The surgeon may then engage the implant 20 with the receptacle 180. In this regard, reference is made to FIGS. 2 and 8. There are a number of alternatives available to the skilled artisan to implement a means for engaging the implant 20 with the receptacle 180. By way of example, the instrument 100 includes one or more spring elements 164, 166 operating to engage the opposing major surfaces (e.g., upper and lower surfaces) of the implant 20. In the present embodiment, each spring element 164, 166 is sized and shaped to engage a respective one of the first and second wedges 152, 156. Each spring element 164, 166 includes a bar (or clamp), such as bar 164A shown in FIG. 8. The rotational force provided by the coils of the spring element 164 urge the bar 164A against the major (e.g., upper) surface of the implant 20. A corresponding bar of the other spring element 166 may be urged against the opposing major (e.g., lower) surface of the implant 20 to secure the implant 20 to the receptacle 180.

In order to set an initial distance between the vertebral contact surfaces 120, 121, the surgeon may make an adjustment as to the position of the assembly 150, the receptacle 180, and the implant 20 relative to the distal ends 118, 119 of the ramps 110, 111. For example, the surgeon may simultaneously slide the first, second, and third wedges 152, 156, 155, and the implant 20, proximally or distally (away from or toward the distal ends 118, 119 of the first and second ramps 110, 111), such that the vertebral contact surfaces 120, 121 of the respective first and second ramps 110, 111 achieve some minimal distance from one another. Notably, the mechanical properties of the ramps 110, 111, and the wedges 152, 156, 155 are such that the initial angle Ai between the ramps 110, 111 remains substantially constant during such positioning.

As shown in FIG. 7A, the distal ends 118, 119 of the first and second ramps 110, 111 may then be inserted into the intervertebral space.

As shown in progression between FIGS. 7A-7B, the respective vertebrae 10, 12 may be distracted using the instrument 100. In particular, the wedge assembly 150, and the implant 20 may be slid distally toward the distal ends 118, 119 of the first and second ramps 110, 111, such that the respective vertebral contact surfaces 120, 121 separate from one another. Simultaneously, the implant 20 is advanced along (and between) the first and second ramps 110, 111 toward the intervertebral space. As the initial height Hi ensures that there is sufficient clearance between the inner surfaces 114, 115 of the ramps 110, 111, there are no significant sheer and/or compressive forces applied to the implant 20 during the sliding process. Further, the mechanical properties of the ramps 110, 111, and the wedges 152, 156, 155 are such that the initial angle Ai between the ramps 110, 111 remains substantially constant during the distraction process.

As shown in progression between FIGS. 7B-7C, the respective vertebrae 10, 12 may be further distracted using the instrument 100 by continuing the sliding of the assembly 150 and implant 20, such that the vertebral contact surfaces 120, 121 of the respective first and second ramps 110, 111 continue to distract the respective vertebral bodies 10, 12. The sliding process continues until the vertebrae 10, 12 are sufficiently distracted to receive the implant 20 into the intervertebral space without compressively loading the implant 20.

The surgeon may disengage the implant 20 from the wedge assembly 150 (particularly from the receptacle 180) by releasing the springs 164, 166.

The surgeon may the simultaneously slide the wedge assembly 150, without the implant 20, proximally, away from the distal ends 118, 119 of the first and second ramps 110, 111, such that the respective vertebral contact surfaces 120, 121 advance toward one another while holding the initial angle Ai therebetween substantially constant. This sliding is continued such that the vertebral contact surfaces 120, 121 of the respective first and second ramps 110, 111 permit the vertebral bodies 10, 12 to compressively load the implant 20. The distal ends 118, 119 of the first and second ramps 110, 111 may then be withdrawn from the intervertebral space.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An instrument for inserting an implant into a vertebral space, comprising:
   first and second ramps, each including: (i) opposing outer and inner surfaces, each extending between proximal and distal ends thereof, and (ii) a vertebral contact surface located at the distal end thereof and in opposing relation to the inner surface thereof;
   a ramp adjustment assembly having multiple elements in sliding contact with one another and being disposed between the inner surfaces of the first and second ramps, the ramp adjustment assembly operating to: (i) establish an initial angle between the vertebral contact surfaces of the respective first and second ramps; (ii) adjust an initial height between the inner surfaces of the respective first and second ramps, by way of sliding at least two of the multiple elements in opposing directions relative to one another, whilst remaining between the first and second ramps whilst remaining between the first and second ramps, the initial height being measured at the ramp adjustment assembly; and (iii) separate the vertebral contact surfaces of the respective first and second ramps, while holding the initial angle and the initial height substantially constant; and
   an implant advancing mechanism operating to advance the implant between the first and second ramps, toward the distal ends of the first and second ramps, and toward and into the vertebral space, whilst the ramp adjustment assembly maintains the first and second ramps in separation.

2. The instrument of claim 1, wherein the ramp adjustment assembly includes first and second wedges, each including: (i) a base side oriented toward the inner surface of a respective one of the first and second ramps, and defining a reference plane, (ii) an incline side defining a sliding plane that is at an acute angle to the reference plane, and (iii) a wedge coupling element operating to slidingly engage the incline side of the other of the first and second wedges, such that the sliding planes of the first and second wedges slide parallel to one another, wherein at least one of the first and second wedges includes a ramp coupling element located proximate to the base side thereof and operating to slidingly engage a respective one of the first and second ramps such that the reference plane slides substantially parallel thereto.

3. The instrument of claim 2, wherein the first and second wedges operate to establish the initial angle between the vertebral contact surfaces of the respective first and second ramps.

4. The instrument of claim 2, wherein sliding the first and second wedges relative to one another along the sliding planes thereof operates to adjust the initial height between the inner surfaces of the respective first and second ramps.

5. The instrument of claim 2, wherein simultaneous sliding advancement of the first and second wedges toward the distal ends of the first and second ramps, by way of the respective ramp coupling elements, separates the vertebral contact surfaces of the respective first and second ramps while holding the initial angle therebetween substantially constant.

6. The instrument of claim 2, wherein:
   a proximal-distal axis is defined by the proximal and distal ends of the first and second ramps;
   each of the sliding planes of the first and second wedges define a normal vector thereto;
   the normal vector of the sliding plane of one of the first and second wedges includes a component directed distally along the proximal-distal axis but no component directed proximally along the proximal-distal axis; and
   the normal vector of the sliding plane of the other of the first and second wedges includes a component directed proximally along the proximal-distal axis but no component directed distally along the proximal-distal axis.

7. The instrument of claim 6, wherein the reference planes, sliding planes, and acute angles of the first and second wedges are designed such that the initial angle between the vertebral contact surfaces of the first and second ramps is between about 0 and 45 degrees.

8. The instrument of claim 7, wherein the initial angle between the vertebral contact surfaces of the first and second ramps is about 11 degrees.

9. The instrument of claim 2, wherein the wedge coupling elements include one or more tongue-and-groove couplings operating to complementarily engage one another such that the incline side of the first wedge slidingly engages the incline side of the second wedge and the sliding planes of the first and second wedges slide parallel to one another.

10. The instrument of claim 2, wherein the ramp coupling elements include one or more tongue-and-groove couplings operating to complementarily engage one another, such that the base side of the first wedge slidingly engages the first ramp, and the base side of the second wedge slidingly engages the second ramp.

11. The instrument of claim 2, wherein:
a proximal-distal axis is defined by the proximal and distal ends of the first and second ramps;
one of the first and second wedges includes a bore extending therethrough in a direction substantially parallel to the proximal-distal axis;
the instrument further comprises: (i) a rod extending through, and slideable within, the bore; and (ii) a stop element disposed at a distal end of the rod and operating to prevent the other of the first and second wedges from moving along the proximal-distal axis with respect to the rod;
an actuator operating to slide the one of the first and second wedges on the rod and along the proximal-distal axis, thereby causing the first and second wedges to move relative to one another along the sliding planes thereof, and to adjust the initial height of the first and second ramps.

12. The instrument of claim 11, wherein the stop element operates to permit the other of the first and second wedges to slide in a direction transverse to the proximal-distal axis in reaction to the actuator sliding the one of the first and second wedges on the rod along the proximal-distal axis.

13. The instrument of claim 12, further comprising one or more tongue-and-groove couplings operating to slidingly connect the stop element and the other of the first and second wedges such that the stop element operates to permit the other of the first and second wedges to slide in the direction transverse to the proximal-distal axis in reaction to the one of the first and second wedges sliding on the rod along the proximal-distal axis.

14. The instrument of claim 13, wherein the one or more tongue-and-groove couplings operate to prevent the other of the first and second wedges from moving away from the stop element proximally or distally along the proximal-distal axis.

15. The instrument of claim 11, wherein the actuator includes:
a threaded portion of the rod; and
a nut in threaded engagement with the threaded portion of the rod such that rotation of the nut advances an engagement element thereof to move the one of the first and second wedges on the rod and along the proximal-distal axis.

16. The instrument of claim 11, further comprising calibration markings on at least one of the first and second wedges providing a calibrated visual indication of the relative movement of the first and second wedges and resultant adjustment of the initial height of the first and second ramps.

17. The instrument of claim 1, wherein the ramp adjustment assembly includes:
first and second ramps, each including: (i) opposing outer and inner surfaces, each extending between proximal and distal ends thereof, and (ii) a vertebral contact surface located at the distal end thereof and in opposing relation to the inner surface thereof;
first and second wedges, each including: (i) a base side oriented toward the inner surface of a respective one of the first and second ramps, and defining a reference plane, (ii) an incline side defining a sliding plane that is at a first acute angle to the reference plane, and (iii) a ramp coupling element located proximate to the base side and operating to slidingly engage a respective one of the first and second ramps such that the reference plane slides substantially parallel thereto; and
a third wedge including: (i) first and second opposing incline sides, each defining a respective first and second sliding plane, which are at a second acute angle with respect to one another, (ii) first and second wedge coupling elements, each operating to slidingly engage a respective one of the incline sides of the first and second wedges, such that the first sliding plane of the third wedge slides parallel to the sliding plane of the first wedge, and such that the second sliding plane of the third wedge slides parallel to the sliding plane of the second wedge.

18. The instrument of claim 1, wherein the separation of the first and second ramps, while maintaining the initial angle therebetween substantially constant, operates to provide parallel distraction of adjacent bodies when the insertion instrument is positioned within an interbody cavity.

19. The instrument of claim 1, wherein the instrument is configured to receive a compressive force, imparted by vertebral bodies adjacent to the intervertebral space, on the first and second ramps, thereby avoiding loading the implant with the compressive force during insertion of the instrument into the intervertebral space.

20. The instrument of claim 1, wherein the instrument operates to discontinue receiving the compressive force imparted by the vertebral bodies once the implant insertion is complete, thereby transferring the compressive force to the implant.

21. The instrument of claim 1, wherein the initial angle is a non-zero angle.

* * * * *

UNITED STATES PATENT AND TRADEMARK OFFICE
CERTIFICATE OF CORRECTION

PATENT NO.        : 8,876,829 B2                                Page 1 of 1
APPLICATION NO.   : 14/025068
DATED             : November 4, 2014
INVENTOR(S)       : Randall F. Lee and Michael J. Mojica It is certified that error appears in the above-identified patent and that said Letters Patent is hereby corrected as shown below:

TITLE PAGE: ITEM (72) SHOULD READ: Randall F. Lee, Arlington, TX (US)
                                   Michael J. Mojica, Englewood, CO (US)

Signed and Sealed this
Seventeenth Day of February, 2015

Michelle K. Lee
*Deputy Director of the United States Patent and Trademark Office*